United States Patent [19]
Bungay et al.

[11] Patent Number: 6,071,727
[45] Date of Patent: Jun. 6, 2000

[54] PRODUCTION OF MICROBIAL CELLULOSE

[75] Inventors: Henry R. Bungay; Gonzalo C. Serafica, both of Troy, N.Y.

[73] Assignee: Rensselaer Polytechnic Institute, Troy, N.Y.

[21] Appl. No.: 08/943,451

[22] Filed: Oct. 3, 1997

Related U.S. Application Data

[63] Continuation-in-part of application No. 08/509,835, Aug. 1, 1995, Pat. No. 5,955,326.

[51] Int. Cl.⁷ .............................. C12P 19/04; C12M 1/10; C08B 15/00
[52] U.S. Cl. .................. 435/101; 435/297.1; 435/297.3; 435/297.5; 435/298.1; 435/299.1; 435/298.2; 536/56; 536/123.1; 536/126
[58] Field of Search ................................... 536/56, 123.1, 536/126; 435/101, 297.1, 297.3, 297.5, 298.1, 299.1, 298.2

[56] References Cited

U.S. PATENT DOCUMENTS

| | | | |
|---|---|---|---|
| 4,320,198 | 3/1982 | Mynatt | 435/101 |
| 4,588,400 | 5/1986 | Ring et al. | 604/304 |
| 4,655,758 | 4/1987 | Ring et al. | 604/374 |
| 4,742,164 | 5/1988 | Iguchi et al. | 536/56 |
| 4,788,146 | 11/1988 | Ring et al. | 435/101 |
| 4,863,565 | 9/1989 | Johnson et al. | 162/150 |
| 4,891,317 | 1/1990 | Brown, Jr. et al. | 435/101 |
| 4,929,550 | 5/1990 | Byrom | 435/101 |
| 4,942,128 | 7/1990 | Brown, Jr. | 435/101 |
| 4,950,597 | 8/1990 | Saxena et al. | 435/101 |
| 4,954,439 | 9/1990 | Brown, Jr. et al. | 435/101 |
| 5,079,162 | 1/1992 | Ben-Bassat et al. | 435/252.1 |
| 5,144,021 | 9/1992 | Arie et al. | 536/56 |
| 5,207,826 | 5/1993 | Westland et al. | 106/163.1 |
| 5,246,854 | 9/1993 | O'Brien et al. | 435/285 |
| 5,256,570 | 10/1993 | Clyde | 435/285 |
| 5,264,129 | 11/1993 | Simpson et al. | 210/611 |
| 5,273,891 | 12/1993 | Byrom | 435/101 |

FOREIGN PATENT DOCUMENTS

| | | | |
|---|---|---|---|
| 1 283 099 | 6/1986 | Canada | C08B 15/00 |
| 1 207 263 | 7/1986 | Canada | A61L 15/01 |
| 1 295 327 | 9/1990 | Canada | C08B 15/00 |
| 62-14787 | 1/1987 | Japan | C12P 1/04 |
| 163664 | 6/1992 | Mexico | C08L 1/002 |
| 2 131 701 | 6/1984 | United Kingdom | A61L 16/03 |

OTHER PUBLICATIONS

American Type Culture Collection, "Catalogue of Bacteria & Bacteriophages," *Bacteria, 17th Edtition*, pp. 1–2 (1989).

Brown, Jr., R. Malcolm, "Emerging Technologies and Future Prospects for Industrialization of Microbially Derived Cellulose," ACS Conference Proceedings Series, *Harnessing Biotechnology for the 21st Century*, American Chemical Society (1992).

Cannon et al., "Biogenesis of Bacterial Cellulose," *Microbiology*, p. 435 (1991).

Lindgren et al., Synthesis of Cellulose by Resting Cells of *Acetobacter xylinum*, Nature, vol. 159, pp. 64–65 (Jan. 11, 1947).

Masaoka et al., Production of Cellulose from Glucose by *Acetobacter xylinum*, Journal of Fermentation and Bioengineering, vol. 75, No. 1, pp. 18–22 (1993).

Sheila Nason, "Sweet Treat or New Textile," *Review*, vol. 16, No. 4, Rensselaer Polytechnic Institute, p. 2 (Feb. 10,1995).

Okiyama et al., Bacterial cellulose 1. Two–stage fermentation process for cellulose production by *Acetobacter aceti*, *Food Hydrocolloids*, vol. 6, No. 5, pp. 471–477 (1992).

Schramm et al., Factors affecting Production of Cellulose at the Air/Liquid Interface of a Culture of *Acetobacter xylinum*, *J. gen. Microbiol.* 11, pp. 123–129 (1954).

Valla et al., "Cellulose–negative Mutant of *Acetobacter xylinum*," *Journal of General Microbiology 128*, pp. 1401–1408 (1982).

White et al., "Prospects for the Commercialization of the Biosynthesis of Microbial Cellulose," Department of Botany, University of Texas, pp. 573–590 (1989).

Toyosaki et al., "Screening of Bacterial Cellulose–producing *Acetobacter* Strains Suitable for Agitated Culture," *Biosci. Biotech. Biochem 59* (8), pp. 1498–1502, (1995).

*Primary Examiner*—Francisco Prats
*Attorney, Agent, or Firm*—Darby & Darby

[57] ABSTRACT

A microbial cellulose with high water content and process for making the microbial cellulose utilizes a rotary disk or linear conveyor bioreactor containing a biological medium and a cellulose producing microorganism are provided.

23 Claims, 8 Drawing Sheets

PRODUCTION OF MICROBIAL CELLULOSE

This application is a continuation-in-part of U.S. patent application Ser. No. 08/509,835, filed Aug. 1, 1995, now U.S. Pat. No. 5,955,326.

FIELD OF INVENTION

This invention relates to methods for producing microbial cellulose pellicle gels, and particularly films. The methods incorporate film bioreactors and particularly a rotary disk bioreactor or a linear conveyor reactor to produce a highly hydrated microbial cellulose product. The linear conveyor bioreactor can produce microbial cellulose in continuous films. The bacterial cellulose may additionally contain additives throughout or in discrete portions of the cohesive pellicles.

BACKGROUND OF THE INVENTION

A number of bacteria, and particularly strains of Acetobacter, can be cultivated to produce bacterial cellulose. In the presence of sugar and oxygen, cells of Acetobacter synthesize cellulose extracellularly in the form of fibrils attached to the cell. The fibrils produced by cells incubated in a static culture intertwine with one another to form a hydrophilic network known as a pellicle. See, U.K. Patent Publication No. 2,131,701. This pellicle forms on the air/liquid interface of the motionless and undisturbed culture which is usually contained in shallow trays. Coherent gel-like microbial cellulose pellicles have many uses such as in wound dressings or paper, after removal of the cells.

Bacterial cellulose can also be produced in traditional stirred or agitated bioreactors. However, a non-pellicular form of bacterial cellulose is typically produced by this type of culturing. This production method is highly susceptible to strain instability which is demonstrated by the cell's loss of ability to produce cellulose and gradual cell overgrowth. Valla et al., Cellulose negative mutants of *Acetobacter xylinum*, Journal of General Microbiology, 128, 1401 (1982). Nevertheless, sustained production of reticulated bacterial cellulose under agitated conditions for over 70 hours with mutagenized and selected strains has been reported by Johnson, U.S. Pat. No. 4,863,565.

Byron, U.S. Pat. No. 5,273,891, disclose a four-step process for producing microbial cellulose in a stirred batch culture. Airlift fermentors, which use air bubbles rather than impellers for mixing, have also been adapted for bacterial cellulose production by Okiyama et al., Bacterial cellulose I: Two-Stage Fermentation Process for Cellulose Production by *Acetobacter aceti, Food Hydrocolloids*, 6, No. 5, 471–477. (1992)).

Film bioreactors have been used in wastewater treatment in which growing cells are attached to a structural element of the reactor to form a film. Cell growth is promoted either by flowing nutrients across the film or by moving the film contained in the structural element into a nutrient filled vessel. Two types of film bioreactors are the trickling filter where the film is stationary and media percolates through the film and the rotating biological contactor (RBC) where the film is cultured on a rotary disk which rotates through the medium.

A third type of film bioreactor has also been used in the production of filamentous fungi. See, Heiland, U.S. Pat. No. 5,246,854. This attached growth biological reactor uses a rotating cylinder to which the filamentous fungi attach while the cylinder is partially submerged in a trough filled with nutrient media.

However, non-static film bioreactors have not been used in the production of microbial cellulose. The use of the film bioreactor, as explained in the present invention, provides highly hydrated pellicular and film forms of microbial cellulose which can be processed in specialized manner, during or after growth because of the processes described herein.

SUMMARY OF THE INVENTION

The present invention contemplates methods for producing microbial cellulose. A microbial cellulose pellicle is produced by culturing cellulose-producing organisms for sustained periods of time under non-static conditions in a film bioreactor. The high rate of production of pellicular microbial cellulose provided by the present invention is surprising considering past studies stating that mixing normally reduces the amount of cellulose produced. Schramm, M. and Hestrin, S., Factors Affecting Production of Cellulose at the Air/Liquid Interface of a culture of *Acetobacter xylinum*, Journal of General Microbiology, 11, 123–129 (1954). Moreover, the high rate of synthesis and highly gelated nature of the microbial cellulose pellicle produced using the bioreactors of the present invention, are entirely unexpected.

One preferred embodiment contemplates a method of production for producing a highly gelated, highly hydrated microbial cellulose pellicle by culturing cellulose-producing organisms for sustained periods of time under non-static conditions in a rotating disk film bioreactor.

In another preferred embodiment, the method includes the step of aerobically incubating a cellulose-producing microorganism on a linear conveyor reactor under non-static conditions. This reactor includes a linear conveyor (preferably an endless loop conveyor) and one or more vessels containing growth medium for the microorganism. The conveyor passes through and exits the growth medium in the vessels.

The present invention further contemplates a highly hydrated microbial cellulose product in a pellicular gel form, and preferably in a film form. The bacterial cellulose pellicle that is produced by a rotating disk film bioreactor and/or linear conveyor reactor has twice the amount of water per unit weight of cellulose as compared to bacterial cellulose pellicles produced by cellulose producing organisms under static conditions. This microbial cellulose pellicle can absorb from about 178 to about 226 times its weight in water and preferably about 200 times its weight in water. It has a highly gelated three dimensional structure, and can be dehydrated (fully or partially and preferably to a major degree) for incorporation into various products, including, but not limited to paper.

The present invention also contemplates a microbial cellulose gel film produced by the method described above and preferably by the linear conveyor reactor, as well as a microbial cellulose gel containing additives, such as, for example, solid polymeric additives distributed in the gel in layers, stripes, bands, a gradient, or the like. The bacterial cellulose film form produced by a linear conveyor and may be a continuous film that may be cut into shapes as desired.

The macroscopic and microscopic characteristics of the microbial cellulose product produced in accordance with the present invention differ from those of microbial cellulose produced under known static conditions. Macroscopically, the cellulose produced by the rotating disk and linear conveyor bioreactors can form a highly gelated film, i.e. from about 20 to 30 mm in thickness, in comparison with the microbial cellulose film formed at the air liquid interface of a static culture cultivated for the same amount of time. This continuous pellicle produced using the reactors of the present invention also has a more open structure allowing a higher water absorption capacity in comparison with the cellulose product obtained under static conditions. Microscopic differences also exist.

DETAILED DESCRIPTION OF THE INVENTION

Figure 1:
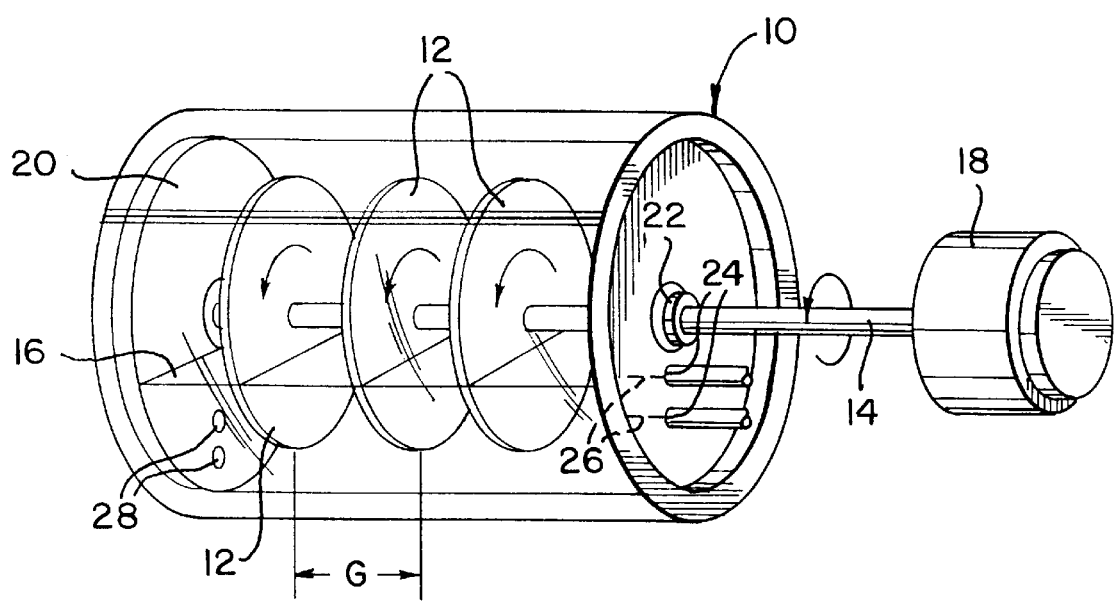
FIG. 1 is a perspective view of one embodiment of the rotating disk film bioreactor with microbial cellulose pellicle forming on the disks, according to the present invention.

The present invention is described with reference to FIGS. 1–4.

The present invention relates to processes for the production of extracellular microbial cellulose in gel and film forms. A bacterial strain capable of producing extra-cellular microbial cellulose is aerobically cultivated in a culture medium containing a carbon source and other nutrients. The culture is incubated on a film bioreactor, such as a rotary disk reactor (1) or a linear conveyor reactor (1A).

The rotary reactor comprises:

a) a series of circular disks (12) (although any shape is possible) with the appropriate mesh size that would allow both the attachment and growth of microbial cellulose producing organisms, and the production of extracellular microbial cellulose; the disks being mounted on a shaft (14) to facilitate rotation;

b) a horizontally disposed trough or vessel (16) (preferably cylindrical) of sufficient length and depth to contain a biological medium in which at least a portion of the contained disks is submerged when enclosed; the covered trough should also have ports (24, 28) to allow media delivery, aeration/oxygen delivery, inoculation, pH monitoring and sampling; and c) an external rotating means (18) attached to the shaft for rotating the disks contained in the trough.

The linear conveyor reactor comprises a linear conveyor (3) and one or more vessels (16, 20). Each vessel (16) contains the same or a different a nutrient growth medium as above. The linear conveyor passes through and exits the medium, bathing the culture in the medium as the conveyor passes through it.

In accordance with the present invention, the method of producing extracellular microbial cellulose by cellulose producing organisms includes one or more of the following:

1) providing a biological reactor as described above;

2) introducing biological medium into one or more vessel or trough;

3) introducing an inoculum of extracellular cellulose producing organism into the vessel trough;

4) rotating the submerged disks in or advancing the linear conveyor through the inoculation containing nutrient and the other medium, if provided, at an effective rate;

5) adding media nutrients, chemicals and polymers, oxygen and monitoring of biological reactor conditions such as pH, whenever necessary; and 6) harvesting the cellulose film formed on the disks or the linear conveyor by appropriate means.

The process of producing microbial cellulose using a bioreactor according to the invention has several advantages over the existing processes and current methods of producing microbial cellulose. These advantages of the present invention include large area available for cellulose production, capability of changing medium conditions during cellulose synthesis, high cellulose production rates, and easy scale up for large volume production of pellicles and gel film of microbial cellulose.

The bioreactors of the present invention allow the forming cellulose film to alternate between periods of immersion in nutrient medium and periods of aeration. This effects a balance of the requirements for air and nutrient so that a uniform microbial cellulose is formed relatively rapidly.

The disk 12 that is used in the biological reactor 10 for the invention has an appropriate mesh size to allow bridging between the two films developing on both sides of the disk or conveyor. It is preferred, for practice of the present invention, that the disk or conveyor be in the form of a mesh or perforated plate, made up of stainless steel or polymeric materials with sufficient rigidity.

The size or diameter of the disk is a selected percentage of the diameter of the cylinder 20 of the reactor 10 that contains the cylindrical biological reactor 10 that contains the disk, with 80% to 90% of the diameter of the cylindrical trough being desirable. The gap between the disks 12 mounted on the shaft 14, labelled "G", is as small as possible to maximize the available area for growth of the cellulose producing organism and production of microbial cellulose by these organisms. The limit of this gap width is the eventual thickness of the bacterial cellulose pellicle at the end of the fermentation.

The cylindrical shape of the biological reactor 1 is chosen to minimize the amount of biological medium required to wet the rotating disk during rotation. Scale up of the rotating disk film bioreactor can be done by increasing either the length of the cylindrical trough or cylinder 20, or the diameter of the cylindrical trough, or both. This correspondingly increases the number of disks 12 and available surface area for cell growth and cellulose production contained in the biological reactor.

The shaft 14 that connects and holds the disks 12 contained in the cylindrical trough 20 is located on the center of the disks but could be along the disk's periphery if there were on assembly of disks. A hermetically sealing bearing 22 is used to connect the shaft 14 to an externally positioned rotating device 18. The preferred rotating means is an electric motor. Any suitable mechanism, such as assortment of gears, to operate several rotating shafts mounted with disks contained in several cylindrical biological reactors, using one motor can be provided for multiple reactor operation. Such a configuration of multiple biological reactors can increase the overall production capacity.

The cylindrical trough 20 of the present invention has openings 24 for the attachment of probes 26 for measurement of reactor conditions such as a pH and temperature. The openings can be located on the lower half of the cylindrical trough 20 containing the biological medium 16. Sample and draining ports 28 are also incorporated in the design. The overall construction of the biological reactor in this invention can be made airtight so as to allow oxygen delivery, thereby maintaining a positive pressure inside the reactor for increased cellulose production (Schramm, et al., 1954) and prevent contamination of non sterile air outside.

The speed of rotation of the disks 12 contained in the biological reactor 10 should be an effective rate which is partially dependent on the diameter of the disk used. Suitable rotational speeds range from 1 rpm to 60 rpm, preferably between 6 to 12 rpm. The rotational speed is usually dependent on the size or diameter of the disk used in the biological reactor. As an example, for a 12 cm. diameter disk, the rotational speed should be between the range of 1 to 30 rpm with 6 to 12 rpm being preferable. The rotational speed of the disks during cellulose production has a noticeable effect on the production rate of cellulose during the fermentation.

Figure 2:
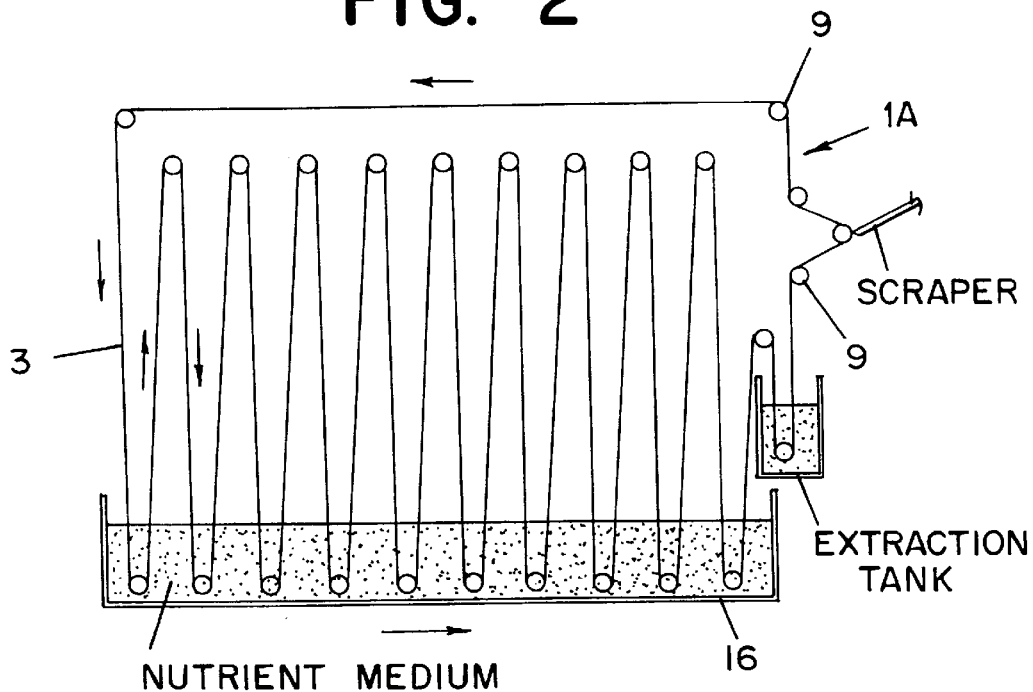
FIG. 2 is a perspective view of one embodiment of the linear conveyor film bioreactor, according to the present invention.
Figure 3:
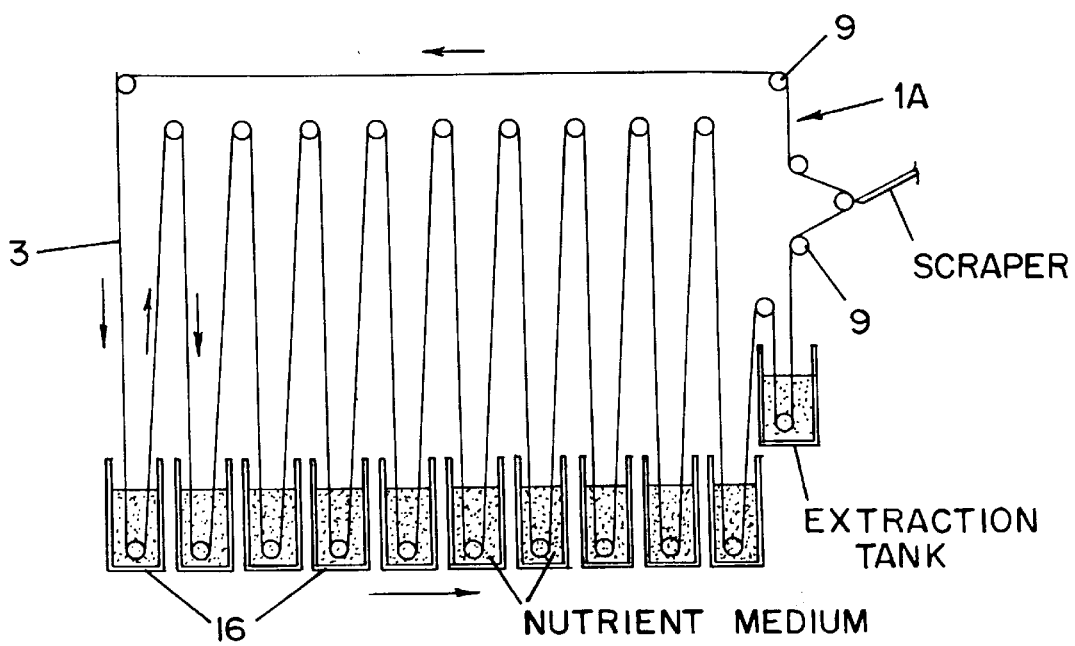
FIG. 3 is a perspective view of a second embodiment of the linear conveyor film bioreactor, according to the present invention.
Figure 4:
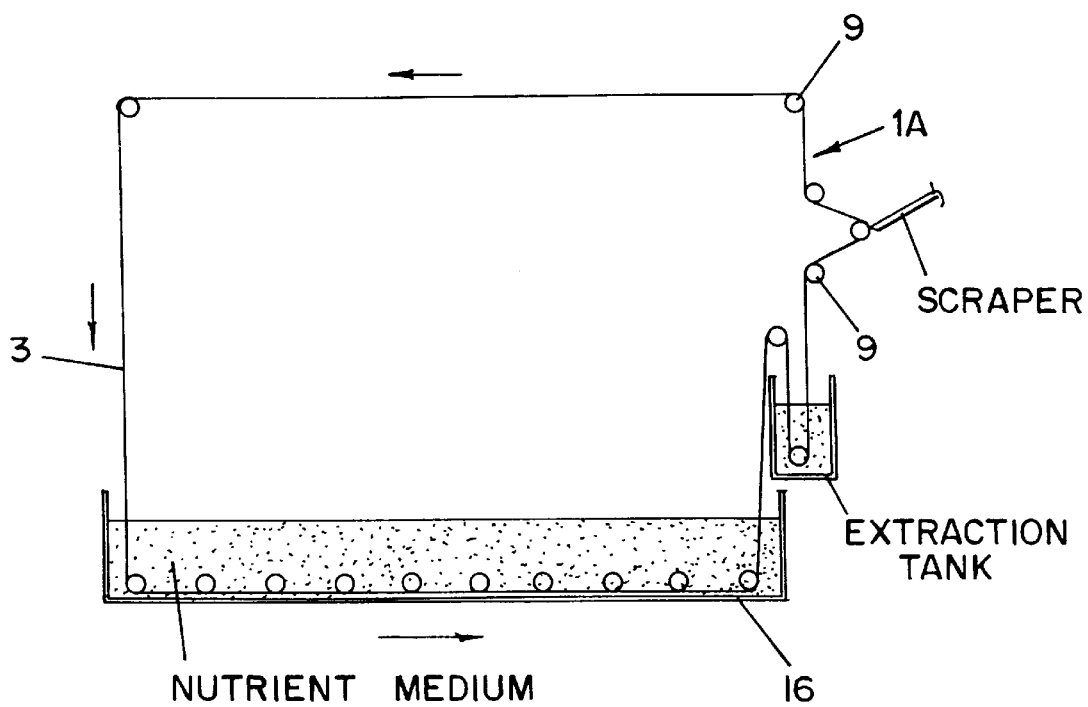
FIG. 4 is a perspective view of a third embodiment of the linear conveyor film bioreactor, according to the present invention.

The linear conveyor is propelled in a machine direction, indicated by the arrows in FIGS. 2–4, preferably on rollers (9) controlled or driven directly or indirectly by an electric motor or the like. Preferably, the linear conveyor is perforated and comprises a mesh like that of the rotary disk bioreactor. The linear speed of the conveyor is usually dependent on the size or depth of the vessels through which the linear conveyor passes.

The growth medium in the linear conveyor reactor can be contained in a single vessel through which the conveyor passes and exits or in multiple vessels through which the conveyor passes and exits in sequence. If the growth medium is contained in a single or multiple vessels, the conveyor may enter and exit each vessel once or more than once. If multiple vessels are used, the growth medium in each vessel may be the same or may differ. Furthermore, if multiple vessels are used, each vessel need not contain growth medium.

The linear conveyor also permits the growth of a continuous film of microbial cellulose, as well as elongated films which may be cut from the template shape of the linear conveyor itself into various lengths and strips.

Additionally, the linear conveyor makes it possible to remove the gel from the conveyor in a continuous manner without interrupting the motion of the conveyor. The gel in both the rotary disk or linear conveyor reactors can be removed, for example by a scraper, a cutter, or a combination thereof.

Multiple vessels permit the adjusting of growth medium at different points of incubation to accommodate the growth dynamics of the forming microbial cellulose gel. For example, pH sugar concentration and the concentrations of other nutrients or additives could easily be adjusted from vessel to vessel without interrupting the incubation process.

The vessels can accommodate the attachment of probes (26) for measurement of reactor conditions such as a pH and temperature. Sample and draining ports (28) in the vessels can also be provided. This reactor can also be made airtight so as to allow oxygen delivery, thereby maintaining a positive pressure inside the reactor for increased cellulose production (Schramm, et al., 1954) and prevent contamination of non sterile air outside.

Additives, such as solids, and particularly polymeric solids, such as, for example, particles of silica gel, aluminum, paper fibers, or carbon, can be incorporated into the gel by passing the linear conveyor through either a growth medium containing vessels which also contain suspended additives or through another vessel containing a suspension of the additive.

The additive in either embodiment can be suspended as necessary by a mixer, such as, for example, an impeller, in the vessel. When the mixer is activated, the additive is suspended and will be incorporated into the passing gel. When the mixer is inactivated, the additive will settle in the vessel, and once the additives settle, they will not be incorporated into the passing gel.

More than one additive can be incorporated by either mixing different additives in a single vessel or providing more than one vessel, each containing a different additive. These two methods may also be combined.

The additive can be an integral part of the gel or a coating.

The rotary disk or linear conveyor reactors can also be arranged to provide the additive(s) in bands, stirpes, or a gradient or in the gel with either multiple vessels, intermittent stirring, or the like. Furthermore, the amount of additive in a single or successive vessels could also be manipulated to vary the amount of additive at different positions in the gel.

The linear conveyor reactor or the rotary disk reactor can also be fitted with sprayers to provide sprays or mists of additional growth medium, coating materials or the like, to the gel when the gel exits a vessel. Additionally, air circulating devices such as, for example fans, can be provided to circulate air or facilitate oxygen transfer to the gel when the gel is not immersed in growth medium.

Additionally, drying or heating devices can be added, such as, for example, a heat oven, a microwave, or a laser can be provided to dry the gel or to fuse any solids in the gel. This heat, microwave, or laser application can be selective at particular sections of the gel or can be used to treat the entire gel. Selective application would be useful in, for example, electronic device production.

The water in a microbial cellulose having a gel/additive layered or the like construction can be driven out of or removed from the construct by, for example, combustion or hydrolysis, to provide sheets of additive or the like that are no longer separated by cellulose. The gel can also pass between rollers to squeeze out a portion of the water so that less water remains in the gel for a subsequent drying step. Similarly, a gel can be passed between rollers to squeeze out residual water that remains after a drying step.

Finally, the microorganisms can be removed from the gel by, for example, washing or the use of sodium hydroxide solution that dilutes the microorganisms from the fibrils. The linear conveyor preferably passes through the microorganism removal stage before removal of excess water or removal of the gel from the conveyor by, for example, a scraper.

A wide range of carbon nutrient sources maybe used including lactate, ethanol, glycerol, molasses, sucrose and other sugars such as fructose and particularly glucose. Suitable initial carbon source concentration are within the range of 0.5 to 100 gm/liter, and preferably 2 to 100 gm/liter. Sugar can be added to the growing culture in the reactor to maintain a certain desirable concentration for optimum cellulose production. For large scale production, various feedstocks for nitrogen sources can utilized including corn steep liquor.

The initial pH at which to cultivate the cellulose producing organism according to the invention is between 3 to 6 with the preferred range of 4.5 to 5.5 and most preferably at 5.0. The pH in the bioreactor can be controlled by means of buffers such as citrate, or by the addition of base or acid to the medium to maintain the pH in the desired range.

The air supply to the reactor can be varied in its composition from air (21% oxygen) to 100% oxygen and in its feed flow rate depending on what is best for the production of microbial cellulose. Maintenance of a positive pressure of oxygen inside the bioreactor to increase rates of production and prevent contamination.

The modes of operating the biological reactors can be by batch fermentation, fed batch fermentation and continuous fermentation, with each having its own advantages. Batch fermentation may be sufficient for producing pellicular microbial cellulose for bulk applications. Fed-batch fermentation or continuous processing may be desirable especially in the production of modified or composite microbial cellulose pellicles.

When operating the biological reactor in fed batch mode, additional medium is introduced into the reactor during the course of the fermentation. Depending on the requirements of the product to be produced in the reactor, the medium composition and condition can be changed accordingly. If a continuous fermentation is desired, after the cellulose film has sufficiently formed on the conveyor, the cellulose produced can scraped off and harvested and the conveyor can complete a loop and return to the vessels. Additional nutrient and inoculum maybe added depending on the demands of the reactor.

The use of rotating disk or linear conveyor film bioreactors has several advantages over the existing processes and methods of producing microbial cellulose. The present invention besides having the ability to produce a pellicular microbial cellulose, has the capability of modifying the cellulose film while it is being synthesized in the bioreactor. By controlling the media conditions and composition, it is not only possible to optimize the cellulose production in the biological reactor but also enables incorporation of different types of polymers/additives to the developing cellulose pellicle. Such modifications in the medium would be very difficult to implement in static systems or agitated systems of cultivation. The addition of polymers/additive to the growing continuous layers of cellulose can more easily be accomplished in the rotating disk or linear conveyor film reactor than in stirred deep-tank bioreactor systems of the prior art.

The formation of cellulose by extracellular cellulose producing organism occurs at the air liquid interface and cellulose production is directly proportional to the area of the said interface (Masaoka, S., Ohe, T. and Sakota, N. Production of Cellulose from Glucose by *Acetobacter xylinum, Journal of Fermentation and Bioengineering,* 74, No. 1, 18–22 (1993)). The present invention provides a large surface area to liquid volume ratio available for bacterial cellulose film growth as compared to static methods of cultivation.

Scale up of the present invention can be accomplished easily by increasing the length of the cylindrical trough or vessels, the number of vessels, the diameter of the disks, or the length or width of the linear conveyor thereby increasing the area for cell growth and cellulose production. The modular nature of the biological reactor described in this invention permits the increase in production capacity by increasing the number of modules/bioreactors in service. Losses due to contamination can also be minimized by this modular design of the present invention.

Any bacterial strain capable of producing extracellular microbial cellulose maybe used in the process of the invention. Suitable strains include strains belonging to the genus Acetobacter, for instance, *Acetobacter xylinum* strains of the species such as ATCC 10245, 23769, and 1082.

The inoculum can be prepared by incubating the extracellular cellulose producing organism obtained from a growing culture on agar slant in a suitable medium at an effective temperature of about 25° C. to 35° C. preferably at 30° C. Incubation times range from three to five days depending on the size of the inoculum used. After incubation, the resulting microbial cellulose pellicle is macerated to release the cellulose producing cells. Prior to its addition to the reactor, the inoculum is usually centrifuged or filtered to separate the cells from the cellulose. The media for the reactor may be separately sterilized in an autoclave under appropriate conditions for an effective period of time to obtain substantial sterilization. The entire biological reactor and the contents can be placed in a temperature controlled room at an appropriate temperature, preferably at 30° C. A sterile oxygen containing gas can be introduced to the reactor during growth of the extracellular cellulose producing organism and production of microbial cellulose by the organism.

The method of the present invention can be used, for example, in the preparation of wound dressings, paper currency optionally with solid inclusions for coding or anti-counterfeiting, and microbial paper optionally with recycled paper particles added.

The microbial cellulose could also incorporate microdevices which could be oriented by, for example, hydraulic means.

In, for example, paper making, much of the water in the microbial cellulose gel can be removed mechanically by squeezing or filtering at one or more stages in the incubation process as the film is supported by the linear conveyor.

DESCRIPTION OF THE PREFERRED EMBODIMENTS

EXAMPLE 1

Comparison of Cellulose Production in Static Cultures and in a Rotating Disk Film Bioreactor (RDFB)

The extracellular cellulose producing microorganism is a strain of Acetobacter xylinum obtained from National Science and Research Institute at University of Philippines, Quezon City, Philippines. The microorganism is maintained on tomato serum broth in agar slants and transferred monthly. The composition of the maintenance culture (TSB) medium is as follows, 50 g/l sucrose or glucose, 5 g/l yeast extract, 5 g/l bactopeptone, 10% v/v tomato serum, Ig/l $K_2HPO_4$, 0.2 g/l $MgSO_4.7H_2O$, and 0.1 g/l NaCl, pH=5. The rate of cellulose production in tomato serum broth (TSB) is checked regularly to make sure no mutation or contamination has occurred.

Seed test tubes containing 25 ml of 50 g/l glucose, 5 g/l bactopeptone, and 5 g/l yeast extract (GYP medium) are inoculated from agar slants. The test tube cultures are grown for three days at 30° C. without shaking and then transferred in a 250 Erlenmeyer flask containing 150 ml of GYP medium. After 3 days of static culture, the seed flasks is used to inoculate both static flask cultures and the rotating disk film reactor at a level of 15% v/v.

Some of the inoculated GYP medium is transferred to the static culture flasks that serve as controls and the rest is used to fill the rotating disk film bioreactor to the halfway mark. Both static and rotated cultures are incubated at 30° C., and samples are taken each day.

Figure 5:
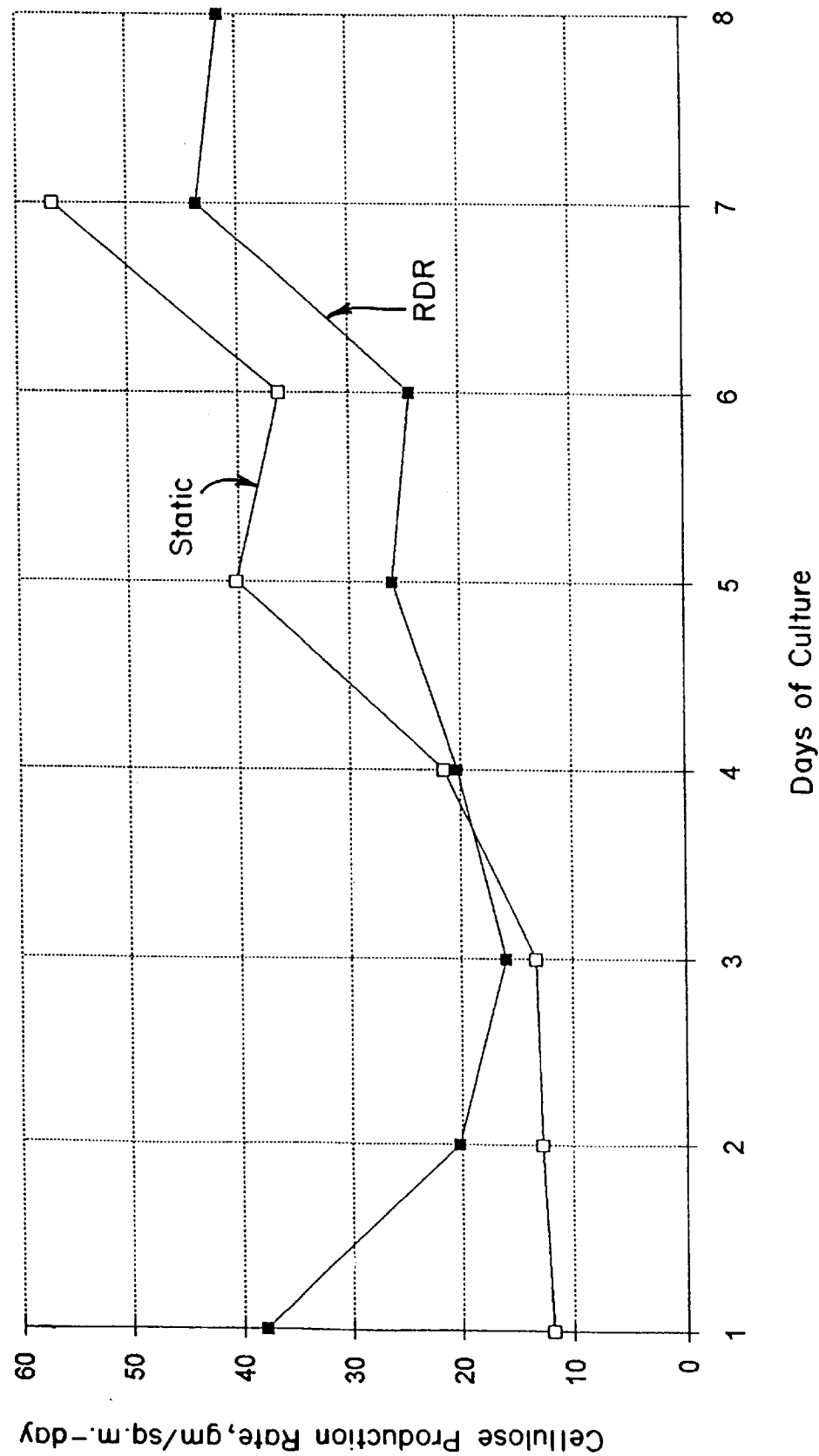
FIG. 5 is a graph showing the linear relation between time of culture and amount of cellulose produced in the rotating disk film bioreactor (RDR) and in a static culture.

To measure the cellulose production, the pellicle in the static culture and the film formed in the rotating disk are harvested and then washed with deionized water. Both are then suspended in a hot 2% NaOH. solution for 30 minutes to disintegrate the cells embedded in the pellicle. The wet cellulose pellicles are then soaked in deionized water until the color becomes white or transparent and then dried overnight at 55° C. The resulting dried cellulose films are weighed (data shown in FIG. 5).

EXAMPLE 2

Comparison of Water Content of Static and Rotating Disk Bioreactor Microbial Cellulose Product The water content of the microbial cellulose produced by the two processes were compared by measuring the wet weight and the dry weight of the two cellulose products. The microbial cellulose pellicles for this study are obtained from a five day old culture using GYP medium. After harvesting the pellicles in both the static and rotating bioreactor, the cellulose products are cleaned using deionized water and 2% NAOH. as previously mentioned.

The wet weight of the microbial cellulose product is measured by draining the water-soaked pellicle for five minutes and then taking the weight. The dry weight is measured after drying the wet pellicle at 55° C. overnight. The results, suggest that typically, microbial cellulose obtained under static conditions has a ratio of dry cellulose to wet cellulose of about 1:100. The microbial cellulose produced by the rotating disk bioreactor has a ratio of 1:200, showing that it is more gelated and has a higher water absorbing capacity than the statically grown pellicle.

| Process | Sample 1 | | Sample 2 | | Sample 3 | |
|---|---|---|---|---|---|---|
| Weight (gms) | Wet | Dry | Wet | Dry | Wet | Dry |
| Static | 16.31 | 0.148 | 37.07 | 0.361 | 84.5 | 0.832 |
| Rotating Disk | 191.4 | 1.07 | 201.9 | 1.08 | 157.6 | 0.696 |

EXAMPLE 3

Effect of Rotational Speed on Cellulose Production in a RDFB

Figure 6:
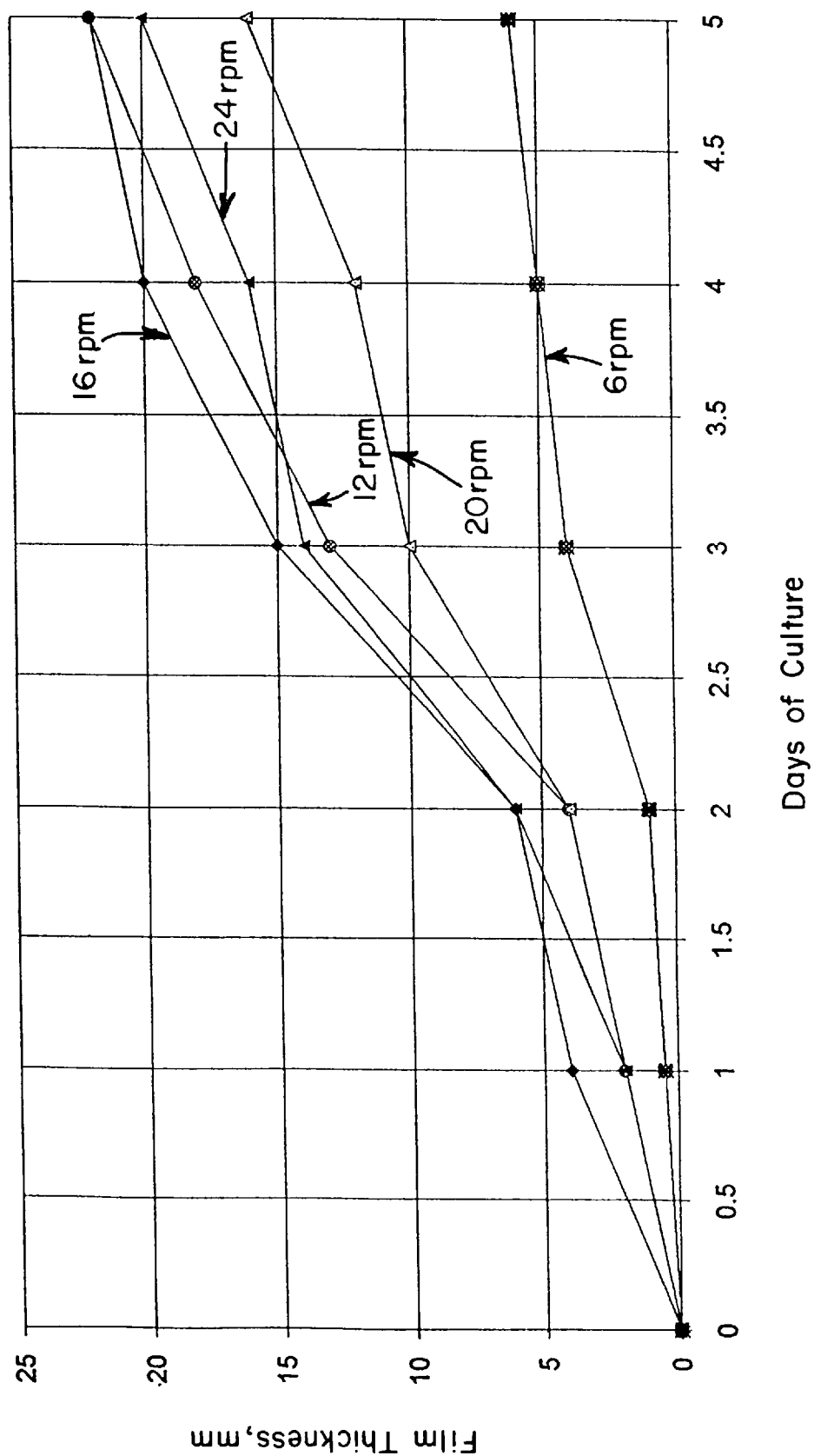
FIG. 6 is a graph showing the effect of rotational speed of the disks in the rotating disk film bioreactor on the production rate of microbial cellulose.

Several 1-liter Rotating Disk Bioreactors were charged with the same inoculated GYP medium and were incubated at 30° C. Each reactor has a different rotational speed falling in the range of 2 to 30 rpm. The thickness of the developing film which is in direct proportion to the amount of cellulose product produced was measured for each rotational speed on a daily basis. The results as shown in FIG. 6, indicate that for the size of the disk used in all the reactors (12 cm. diameter), the speed of rotation displaying fast film growth is between 12 to 20 rpm, preferably 12 rpm. Although an optimum speed for a 12 cm disk was found, such desirable rotational speed may vary depending on the size of the disk being used. Calculating the peripheral velocity of each disk size can help in determining the appropriate rotational speed for a given size of disk.

EXAMPLE 4

Effect of Different Initial Sugar Concentration on Cellulose Production

Figure 7:
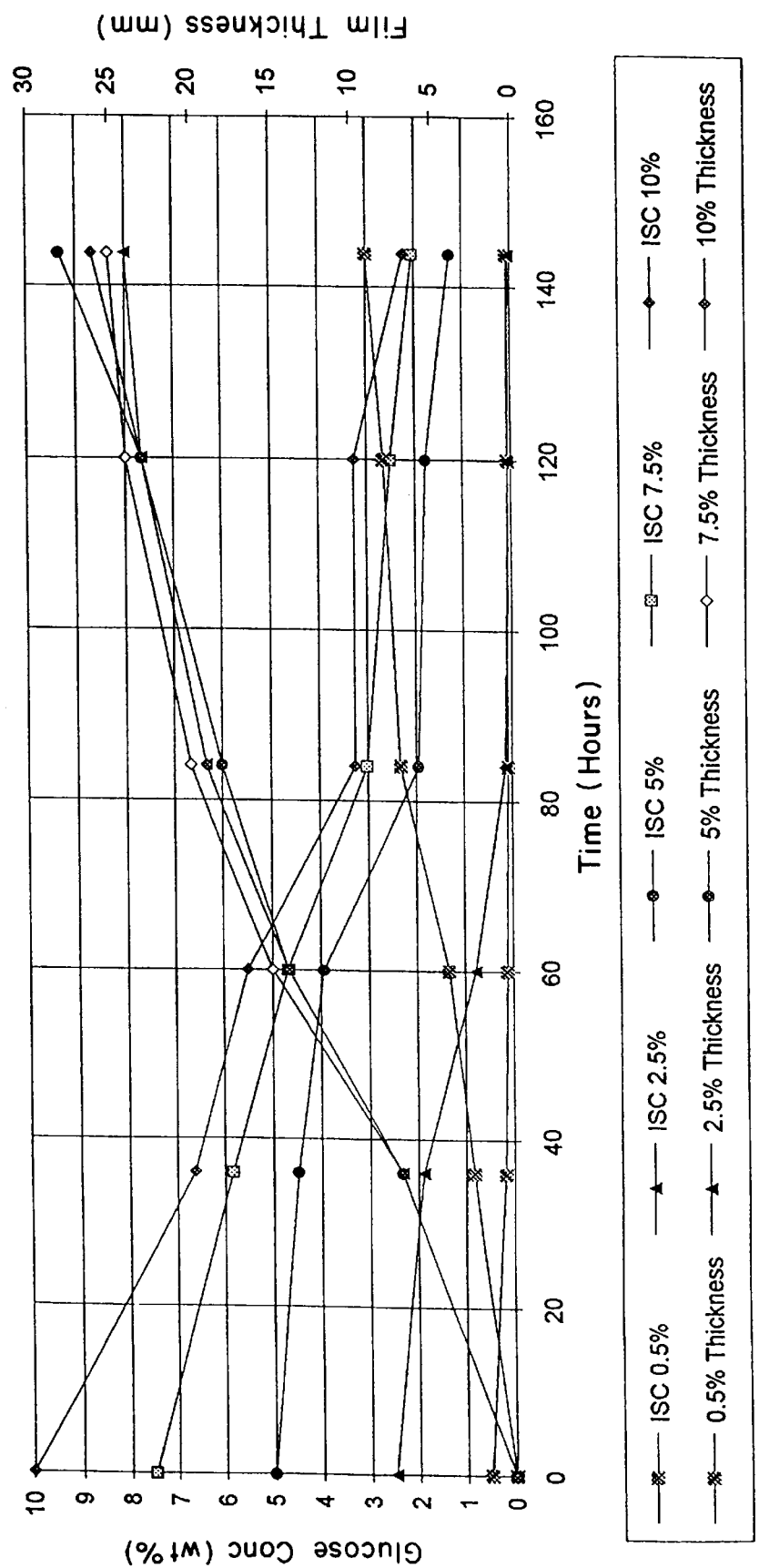
FIG. 7 is a graph showing the effect of initial sugar concentration in the rotating disk film bioreactor on the production rate of microbial cellulose.

The effect of starting sugar concentration in the medium on cellulose production in a batch rotating disk bioreactor was studied. Several reactors containing medium with different initial sugar concentration ranging from 5 g/l to 100 g/l were operated for five days. With all other components being the same, the rate of production of cellulose was compared in each bioreactor by measuring the thickness of the film developed in the disks. As previously mentioned, the film thickness is directly proportional to the amount of cellulose produced. In FIG. 7, the results showed that above 25 g/l, increasing the sugar concentration does not correspond to an increase in cellulose production during the five day culturing time. However, an inadequate amount of sugar as in the case of 5 g/l, can hamper cellulose production. Therefore, in order to maximize the amount of cellulose produced, a certain amount of sugar concentration should be maintained in the bioreactor all through the fermentation. Such a maintenance sugar concentration lies between 5 g/l and 25 g/l.

EXAMPLE 5

Figure 8:
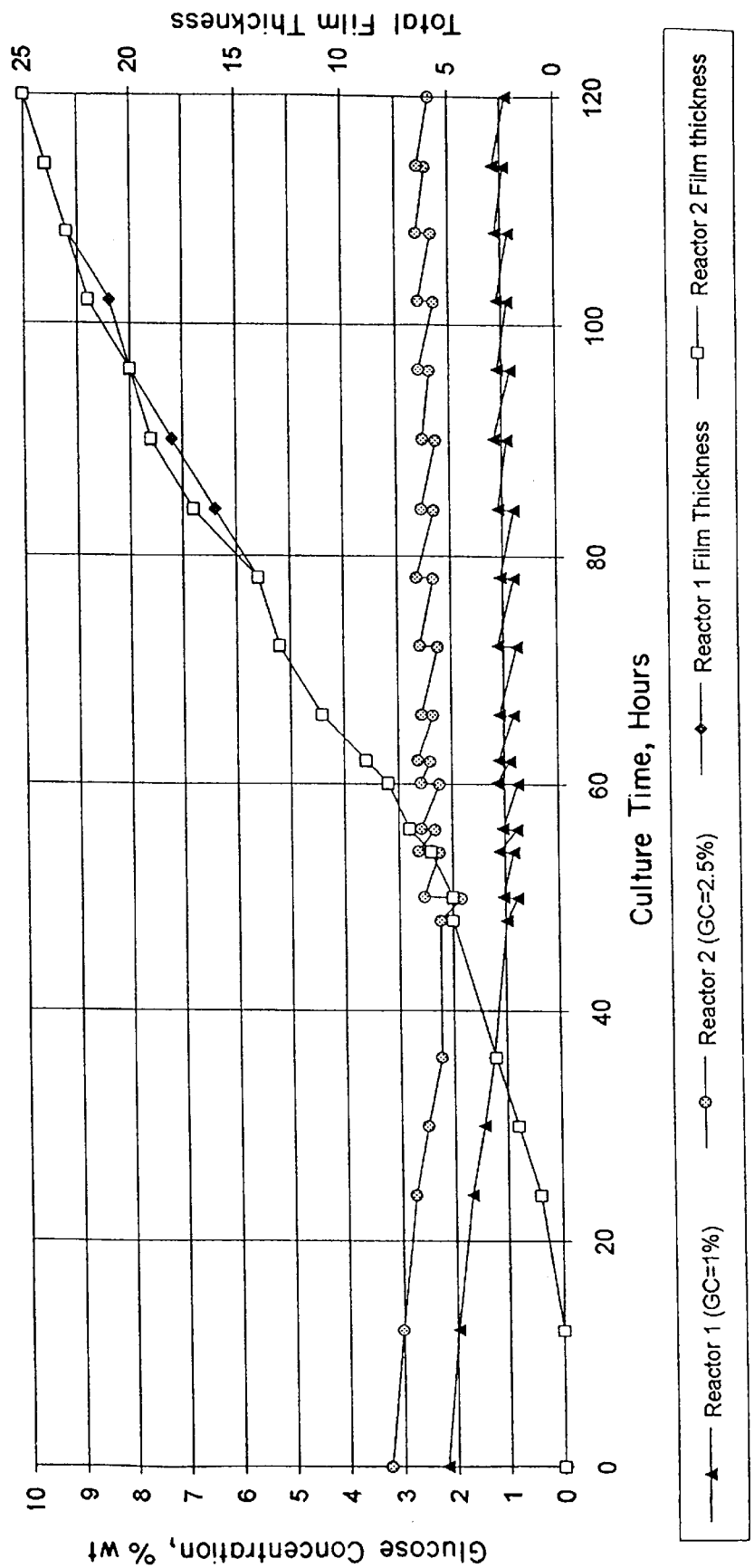
FIG. 8 is a graph of sugar concentration and cellulose film growth during a Fed batch operation of the rotating disk bioreactor.

Fed Batch Operation of the Rotating Disk Bioreactor with Control of Sugar Concentration The rotating disk bioreactor is operated in fed-batch mode wherein sugar is added during the course of the fermentation in order to maintain a certain level of sugar concentration in the reactor. For our purpose, two reactors are operated simultaneously, one having a maintained sugar concentration of 25 g/l and the other at 10 g/l. The sugar concentrations are monitored using a YSI glucose analyzer. Based on the two runs performed (FIG. 8), similar cellulose production rates are observed for both maintained concentration as shown by almost similar rate of film growth on the disks. In order to reduce the amount of sugar wasted, thereby increasing the yield of cellulose per gm of sugar, a concentration of 10 g/l in the bioreactor is preferred.

EXAMPLE 6

Figure 9:
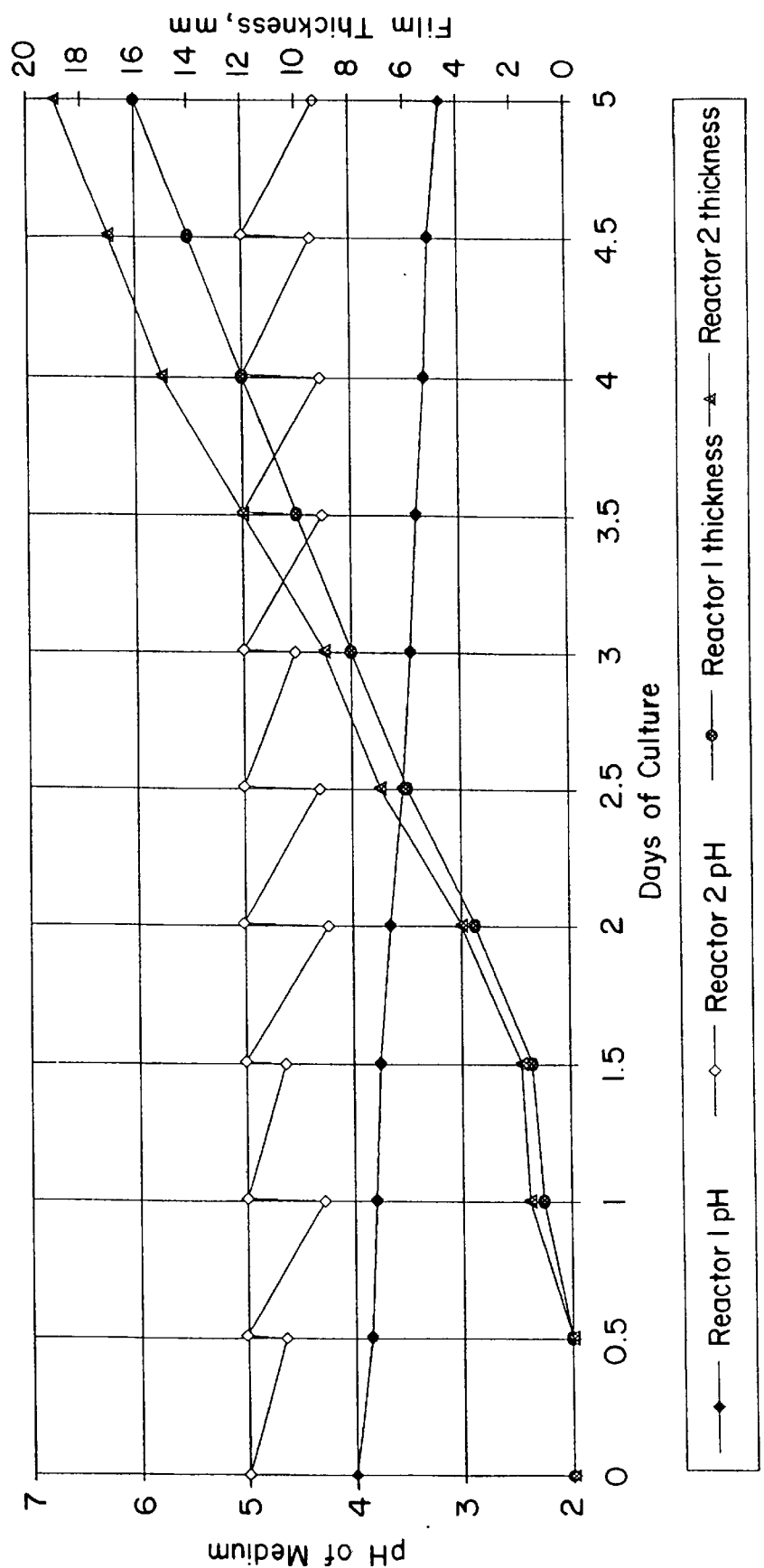
FIG. 9 is a graph showing the effect of operating pH on cellulose production during batch operation of the rotating disk bioreactor.

Effect of Operating pH on Cellulose Production During Batch Operation of the Rotating Disk Bioreactor The rate of cellulose production is very much affected by the operating pH of the medium (Masaoka, 1993). In order to show this effect in the bioreactor, two 1 l rotating disk bioreactors are operated simultaneously, one having a pH maintained at pH 5 and the other without pH control. The pH adjustment is accomplished by the addition of base like dilute NAOH. during the fermentation run. The measured rate of film growth is used to indicate the rate of cellulose production as done previously. From FIG. 9, the results show that higher cellulose production can be obtained by maintaining the operating pH in the reactor at the desirable level such as pH 5.

While a specific embodiment of the invention has been shown and described in detail to illustrate the application of the principles of the invention, it will be understood that the invention may be embodied otherwise without departing from such principles.

All patents, applications, publications, and test methods mentioned herein are hereby incorporated by reference. Many variations of the present invention will suggest themselves to those skilled in this art in light of the detailed description herein. All such obvious variations are within the full intended scope of the claims appended hereto.

We claim:

1. Pellicular microbial cellulose having a cellulose:water absorbed weight ratio ranging from about 1:178 to about 1:226.

2. Pellicular microbial cellulose as defined in claim 1, wherein said ratio is 1:200.

3. Pellicular microbial cellulose as defined in claim 1, having an additive incorporated therein.

4. Pellicular microbial cellulose as defined in claim 1, having a polymer incorporated therein.

5. Highly hydrated microbial cellulose having a cellulose:water absorbed weight ratio ranging from about 1:178 to about 1:226, produced by (a) aerobically incubating a medium containing a cellulose producing microorganism in a rotating disk bioreactor.

6. Highly hydrated microbial cellulose as defined in claim 5, wherein said microorganism belongs to the genus Acetobacter.

7. Highly hydrated microbial cellulose as defined in claim 6, wherein said microorganism belongs to the species *Acetobacter xylinium*.

8. Highly hydrated microbial cellulose as defined in claim 7, wherein said microorganism is selected from the group consisting of *Acetobacter xylinium* strains ATCC 10245, ATCC 23769, and ATCC 2082.

9. Highly hydrated microbial cellulose as defined in claim 5, having an additive incorporated therein.

10. Highly hydrated microbial cellulose as defined in claim 5, having a polymer incorporated therein.

11. Highly hydrated microbial cellulose having a cellulose:water absorbed weight ratio ranging from about 1:178 to about 1:226.

12. Highly hydrated microbial cellulose as defined in claim 6, wherein said ratio is 1:200.

13. Highly hydrated microbial cellulose as defined in claim 11, having an additive incorporated therein.

14. Highly hydrated microbial cellulose as defined in claim 11, having a polymer incorporated therein.

15. Pellicular microbial cellulose produced by aerobically incubating a medium containing a cellulose producing microorganism in a rotating disk bioreactor wherein said microbial cellulose gel film has a cellulose:water absorbed weight ratio ranging from about 1:178 to about 1:226, and is capable of being fully or partially dehydrated.

16. Pellicular microbial cellulose as defined in claim 15, wherein said ratio is 1:200.

17. A microbial cellulose gel film produced by aerobically incubating a cellulose-producing microorganism on a linear conveyor reactor comprising a linear conveyor and one or more vessels containing growth medium, said linear conveyor passing through and exiting said growth medium contained in one or more vessels, wherein said microbial cellulose gel film has a cellulose:water absorbed weight ratio ranging from about 1:178 to about 1:226, and is capable of being fully or partially dehydrated.

18. A microbial cellulose gel film as defined in claim 17, having a cellulose:water absorbed weight ratio ranging from about 1:178 to about 1:226.

19. A microbial cellulose gel film as defined in claim 18, wherein said ratio is 1:200.

20. A microbial cellulose gel film as defined in claim 17, having a cellulose:water absorbed weight ratio ranging from about 1:178 to about 1:226, wherein said gel film contains additives and one or more of said vessels further contains an additive to be incorporated into said film.

21. A microbial cellulose gel film as defined in claim 20, wherein said ratio is 1:200.

22. A microbial cellulose gel film as defined in claim 17, having a cellulose:water absorbed weight ratio ranging from about 1:178 to about 1:226.

23. A microbial cellulose gel film as defined in claim 22, wherein said ratio is 1:200.

* * * * *